United States Patent [19]

Dunks et al.

[11] 4,100,199

[45] Jul. 11, 1978

[54] CARBORANE PURIFICATION

[75] Inventors: Gary Burr Dunks, Peekskill; Kathy Palmer Ordonez, Scarsdale, both of N.Y.

[73] Assignee: Union Carbide Corporation, New York, N.Y.

[21] Appl. No.: 761,212

[22] Filed: Jan. 21, 1977

[51] Int. Cl.$^2$ ............................................. C07F 5/02
[52] U.S. Cl. ............................................. 260/606.5 B
[58] Field of Search ................................. 260/606.5 B

[56] References Cited

U.S. PATENT DOCUMENTS

| | | | |
|---|---|---|---|
| 3,030,422 | 4/1962 | Clark et al. | 260/606.5 B |
| 3,201,450 | 8/1965 | Cohen et al. | 260/606.5 B |
| 3,247,256 | 4/1966 | Fein et al. | 260/606.5 B |
| 3,287,416 | 11/1966 | Bobinski et al. | 260/606.5 B |
| 3,463,820 | 8/1969 | Ager et al. | 260/606.5 B |
| 3,483,258 | 12/1969 | Fein et al. | 260/606.5 B |
| 3,505,409 | 4/1970 | Bobinski et al. | 260/606.5 B |

OTHER PUBLICATIONS

Fein et al., Inorg. Chem. V 2, pp. 1115–1119 (1963).
Heying et al., Inorg. Chem. 2, pp. 1089–1092 (1963).
Fein et al., Inorg. Chem., V 2, pp. 1111–1115 (1963).

*Primary Examiner*—Helen M. S. Sneed
*Attorney, Agent, or Firm*—William Raymond Moran

[57] ABSTRACT

A simple, efficient and safe method is provided for the separation of carborane products such as 1,2-dicarba-closo-dodecaborane(12), 1-bromomethyl-1,2-dicarba-closo-dodecaborane(12), 1-(n-hexyl)-1,2-dicarba-closo-dodecaborane(12) and various other substituted carborane derivatives from tarry materials present in their reaction mixtures. The method involves dissolving the reaction mixture in a solvent in which all of the components of the reaction are very soluble and non-reactive, and thereafter extracting the solution with a second solvent which is non-reactive and immiscible with the first solvent, and in which side products are insoluble but the desired carborane product is selectively soluble. The purified carborane products have a variety of uses, particularly as intermediates for other products having known utility.

17 Claims, No Drawings

CARBORANE PURIFICATION

This invention relates in general to a process for the purification of carborane products. In one aspect this invention relates to a process for the separation of carborane products from tarry materials present in their reaction mixtures. In a further aspect, this invention is directed to a process for the purification of carboranes, such as 1-(n-hexyl)-1,2-dicarba-closo-dodecaborane(12), 1-(n-$C_6H_{13}$)-1,2-$C_2B_{10}H_{11}$).

Prior to the present invention the literature disclosed various methods for the synthesis of carboranes and their derivatives. For example, it has been found that the procedure for the synthesis of carboranes, such as 1,2-dicarba-closo-dodecaborane(12), (1,2-$C_2B_{10}H_{12}$), 1-bromomethyl-1,2-dicarba-closo-dodecaborane(12), (1-$BrCH_2$-1,2-$C_2B_{10}H_{11}$) and various other substituted carborane derivatives from decarborane and the appropriate acetylene have been described in numerous papers. In all instances, the carborane product must be separated from tarry side products formed as a result of the particular reaction employed. The tarry material may contain reactive substances which can render the known separation methods hazardous and, hence, require especial precautions in preparation of the carborane product.

For instance, the separation of 1,2-$C_2B_{10}H_{12}$ requires a long pre-treatment of the reaction mixture with acetone, methanol and hydrochloric acid followed by its addition to 11-16 volumes of water maintained at or near boiling. The volatile components, including a significant amount of 1,2-$C_2B_{10}H_{12}$, are then distilled off and the water soluble materials remain dissolved in the water. The major fraction of the water-insoluble 1,2-$C_2B_{10}H_{12}$ remains on the surface of the water and is skimmed off. This entire procedure is undesirable in that copious quantities of noxious fumes are produced and the hot aqueous mixture has been known to inflame as cited by M. F. Hawthorne, et al, *Inorganic Synthesis*, 10, 91 (1967). After drying to remove water and extraction of the resulting solid with n-heptane, the 1,2-$C_2B_{10}H_{12}$ is isolated from the n-heptane. The published yield as reported in the literature using this procedure is 72 percent of theory as cited supra, pages 95 - 100.

The substituted derivatives of 1,2-$C_2B_{10}H_{12}$ are generally separated from the tarry side products by repeated trituration using n-pentane or mixed hexanes. Complete extraction of the carborane product is difficult, time consuming, requires manipulation and the tarry residue may become solid so that scale-up of this procedure becomes economically questionable.

In contrast, the present invention provides a unique method of separating carborane and its substituted derivatives from their respective reaction mixtures, which is efficient, safe, can proceed unattended, can be scaled-up, and avoids many of the hazards associated with the processes reported in the literature. Prior to the present invention it was not possible to provide a simple, safe process for the separation and purification of carboranes from their tarry reaction products. As carboranes become increasingly important in industrial applications it is imperative that safe and efficient methods of synthesis and purification be employed.

Accordingly, one or more of the following objects will be achieved by the practice of the process of this invention. It is an object of this invention to provide an improved and efficient process for the separation of carboranes and derivatives thereof from their reaction mixtures.

Another object of this invention is to provide a process for the separation of carbonate products from their reaction mixture which is safe and avoids many of the hazards associated with prior art processes. A further object is to provide a process which employs two or more solvents for the separation of the desired carborane products. A still further object of the invention is to provide a process which utilizes a solvent in which the desired carborane product is preferentially soluble and side products and undesirable tarry residues are insoluble. Another object of this invention it to provide a safe and efficient process for the separation and purification of carboranes, such as 1-(n-hexyl)-1,2-dicarba-closo-dodecaborane(12). These and other objects will readily become apparent to those skilled in the art in the light of the teachings herein disclosed.

In its broad aspect, this invention is directed to a process for the separation and purification of carboranes from a reaction mixture comprised of the carborane and undesirable tarry by-product formed during the reaction of decaborane, ($B_{10}H_{14}$), with an acetylenic compound in the presence of a donor ligand. The process comprises the steps of:

(a) removing from the mixture any solvent in which the carborane was synthesized except when such solvent:

(i) also serves as the donor ligand (ii) is employed in an amount in excess of the stoichiometric amount required for the reaction, and (iii) is selected from the group consisting of acetonitrile and propionitrile, (b) dissolving the mixture from which any solvent has been removed in accordance with step (a) in a first solvent in which all the components of the mixture are soluble and non-reactive therewith, (c) extracting the carborane from the mixture with a second solvent, immiscible with the solvent of either step (a) or (b) and in which the carborane is soluble and the by-products are insoluble, and (d) thereafter recovering the carborane from the second solvent.

As previously indicated, the process of the present invention is simple, efficient and provides the desired carborane product with a minimum of hazardous operations. The process is of particular interest for the separation of n-alkyl carboranes from undesirable reaction products formed during their synthesis. For example, 1-(n-hexyl)-1,2-dicarba-closo-dodecaborane(12) is conveniently separated in a relatively high yield by the technique of this invention.

As illustrated by the examples, the process, in general, consists of dissolving the tarry reaction mixture in a first solvent in which all of the components of the reaction are very soluble and non-reactive, and extracting the carborane product with a second solvent, immiscible with the first solvent and in which undesired side products are insoluble. In certain instances, and depending upon the choice of solvent employed, the solvent in which the carborane was synthesized can itself serve as the first solvent in step (b) above. This avoids the necessity for its removal.

For example, the reaction for the synthesis of the carboranes can be illustrated by the following equations:

1. $B_{10}H_{14} + 2L \rightarrow B_{10}H_{12}L_2 + H_2$

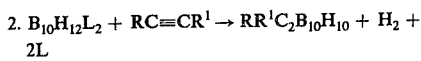

wherein L represents a donor ligand such as acetonitrile, propionitile, diethylsulfide, and the like, and R and $R^1$ represent hydrogen, alkyl, aryl, aralkyl, alkaryl and the like of up to 12 carbon atoms, and need not be identical in the same molecule.

The overall equation that is, the addition of equations 1) and 2) above, is thus as follows:

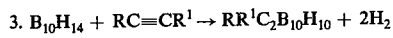

wherein R and $R^1$ are as indicated.

Hence, if the donor ligand is itself one in which all the reaction products are soluble and non-reactive, and if it is immiscible with the second or extracting solvent it can also serve as the reaction solvent when used in excess of the stoichiometric amount. In such instances it is preferred to employ the donor ligand in an amount at least twice that of the required stoichiometric amount.

The optimum system consists of acetonitrile as the first solvent and a lower alkane alone or in admixture with one or more other alkanes, as the second solvent. Subsequent to the extraction the layers are separated and the alkane solution of the carborane is evaporated. Solid carborane products such as $1,2\text{-}C_2B_{10}H_{12}$ can be crystallized from the concentrated alkane solution. In the case of liquid carboranes such as $1\text{-}(n\text{-}C_6H_{13})\text{-}1,2\text{-}C_2B_{12}H_{11}$ the product can be separated from the solvent by distillation. Identification of the desired products was confirmed by appropriate analysis. Separation of the two immiscible liquids can be achieved by methods well-known to those skilled in the art.

As previously indicated, the purification process of this invention can be effected in most any solvent which is inert to the products. For example, any solvent system which satisfies the criteria set out above could be used to practice this procedure. The optimum system consists of acetonitrile ($CH_3CN$) as the first solvent and a lower aklane ($C_4\text{-}C_7$) or mixtures of lower alkanes as the extractment. Subsequent to the extraction the layers are separated and the alkane solution of the carborane is evaporated. Solid carborane products such as $1,2\text{-}C_2B_{10}H_{12}$ can be recovered form the concentrated alkane solution. In the case of liquid carboranes such as $1\text{-}(n\text{-}C_6H_{13})\text{-}1,2\text{-}C_2B_{10}H_{11}$ the product can be separated from the solvent by distillation. Other solvents, which accomplish the same result can be employed.

Illustrative other solvent systems which can be employed in the process of this invention but are less preferred include, among others, solvent pairs such as, propionitrile and n-decane; propionitrile and cyclohexane; propionitrile and carbon disulfide; acetonylacetone and n-butane; acetonylacetone and n-hexane; acetonylacetone and n-decane; acrylonitrile and n-hexane; acrylonitrile and n-octane; and the like.

The relative volume of the solvent pair employed in the process of this invention is not necessarily critical and can vary over a wide range, provided, however, that sufficient solvent is used to completely dissolve the residue and sufficient extractant is used to accommodate the carborane product at the particular temperature employed.

A wide variety of temperatures can be used in the separation process of this invention. It is important, however, that the solvent pair remain immiscible at the temperature at which the process is practiced. Additionally, the solvents must remain in the liquid state during separation and be inert towards the residue or desired carborane product. In practice, it has been found that the temperature employed can generally range from about $-10°$ C to about 140° C., depending, of course, on the particular reactants and solvent system used. Temperatures of from about 0° C. to about 100° C. are preferred.

Pressure is not critical and atmospheric, subatmospheric or superatomospheric pressures can be employed as long as the solvents remain immiscible and in the liquid state.

In general, it has been observed that the process of this invention can be utilized in the separation or purification of numerous carboranes and their substituted derivatives. For instance, 1,2-dicarba-closo-dodecaborane(12), as well as the alkyl, aryl, dialkyl, haloalkyl, haloaryl substituted carboranes can be purified by the process of this invention. In addition to 1,2-dicarba-closo-dodecarborane(12), illustrative other carboranes include the 1-alkyl, and di(1,2-dialkyl)substituted carboranes wherein the alkyl groups contain from 1 to about 12 carbon atoms. Examples of such carboranes include methyl-, ethyl-, propyl-, hexyl-, heptyl-, decyl-, lauryl-, dimethyl-, dipropyl-, dihexyl-substituted carboranes. Also illustrative, are the aryl, 1,2-(diaryl), and 1,2-(aryl-lower alkyl) substituted carboranes. For example, such carboranes include phenyl-, diphenyl-, tolyl-, phenylmethyl substituted carboranes.

The halogen substituted alkyl and aryl carboranes are also typical of those carboranes which can be separated by the process of this invention. Examples include 1-bromomethyl-1,2-dicarba-closo-dodecaborane(12), 1-(4-chlorophenyl)-1,2-dicarba-closo-dodecarborane(12) and the like.

The following examples illustrate at least one of the best modes presently contemplated for conducting the process of this invention.

EXAMPLE I

Purification of 1,2-Dicarba-closo-dodecarborane (12)

A 1000-ml, three-necked flask was equipped with an efficient blade stirrer, an inlet tube reaching as near to the bottom of the flask as possible, and an adapter for installing a thermometer and a water-cooled condenser. A heating mantle and a constant temperature controller were used. The system was thoroughly dried and flushed with nitrogen before the reagents were introduced.

Decaborane (100g 0.816 mol) and dibutyl ether (200 ml) were added to the reaction flask. Diethyl sulfide (220 ml) was added in one portion. The solution was stirred for three hours at 40±1° C. with a nitrogen purge. The temperature was then raised to 65±1° C. for two additional hours. The flask was then heated to a controlled temperature of 85±1° C. and excess acetylene (10 mol) was passed through the reaction vessel over a period of 45 hours. After cooling, the solvents were removed in vacuo leaving a pale orange semisolid.

The product was dissolved in 400 ml of acetonitrile and continuously extracted with hexane for 48 hours. Most of the hexane was then distilled off at atmospheric pressure and the residual solvent was removed in vacuo to give a yellow solid. The product, 1,2-dicarba-closo-dodecaborane (12), was purified by sublimation (bath temperature 85° C., 0.005mmHg) and weighed 90g (76%). The purity was estimated by nmr, ir, and glpc to be in the 95–97% range.

The acetonitrile layer was transferred to a 1000 ml flask and placed on a rotary evaporator. Removal of solvent gave 39g of residual oil; 340 ml of acetonitrile was recovered.

EXAMPLE 2

Purification of 1-(n-hexyl)-1, 2-Dicarba-closo-dodecaborane (12)

A 500-ml, three-neck flask fitted with a mechanical stirrer, reflux condenser topped with a nitrogen inlet and a pressure equalized dropping funnel was charged with 30.0g (0.245 mol) of decaborane and 225 ml of benzene. Acetonitrile (20.1g, 0.49 mol) was added over a 20 minute period. The solution was heated to reflux and maintained for 23 hours. The reaction mixture was cooled slightly and 29.7g (0.27 mol) of 1-octyne was placed into the dropping funnel. The reaction mixture was again heated to reflux and the 1-octyne was added over 5.3 hours, with reflux maintained an additional 15 hours.

The mixture was cooled to ambient and the solvents were stripped using a rotary evaporator and 60° C. water bath leaving a viscous red-brown oil (83.5g). The oil was dissolved in 140 ml of acetonitrile and extracted with 1300 ml of hexane for 18 hours. The hexane-carborane fraction was washed with 200 ml of cold water followed by four 250-ml portions of cold 10% NaOH and two 250-ml portions of water. The hexane-carborane fraction was dried over anhydrous $MgSO_4$ and filtered. The solvent was stripped using a rotary evaporator (mechanical pump) and water bath. The residual oil was heated at 240° C for 6 hours under nitrogen followed by distillation (0.5mmHg, 129°) with flask temperature 182°–188° C. to collect 20.1g (0.088 mol, 36%) of $1\text{-}(n\text{-}C_6H_{13})\text{-}1,2\text{-}C_2B_{10}H_{11}$.

EXAMPLE 3

Purification of 1-($\alpha$-Bromohexyl)-1,2-dicarba-closo-dodecaborane(12), $[1\text{-}(\alpha\text{-}BrC_6H_{12})\text{-}1,2\text{-}C_2B_{10}H_{11}]$ A 500-ml, three-necked flask was equipped with mechanical stirring, reflux condenser, nitrogen inlet, and an addition funnel. Decarborane (12.2g, 0.1 mol) and acetonitrile (75 ml) were placed in the reaction flask and the mixture was heated at reflux for four hours. A granular solid separated from the solution. 3-Bromo-1-octyne (20.0g, 0.105 mol) was added dropwise over 30 minutes. The reaction mixture was heated to reflux for 20 hours. After cooling to room temperature, the acetonitrile solution was transferred to a separatory funnel and extracted with three 100 ml portions of hexane.

The hexane solution was washed with a 5% sodium hydroxide solution, a 5% hydrochloric acid solution, and with a saturated sodium chloride solution, and dried over magnesium sulfate. After filtration, the hexane solution of 1-($\alpha$-bromohexyl)-1,2-dicarba-closo-dodecaborane(12) was filtered through a pad (1 inch) of neutral alumina (Activity I) on a fritted glass filter. Evaporation of the solvent yielded 28.1g (91%) of 1-($\alpha$-bromohexyl)-1,2-dicarba-closo-dodecaborane(12).

EXAMPLE 4

Purification of 1-Phenyl-1,2-dicarba-closo-dodecaborane(12), $[1\text{-}C_6H_5\text{-}1,2\text{-}C_2B_{10}H_{11}]$ A 500-ml, three-necked flask is equipped with a mechanical stirrer, reflux condenser, nitrogen inlet and an addition funnel. Decarborane (11.0g, 0.09 mol), acetonitrile (75 ml) and benzene (50 ml) are placed in the flask and the mixture is heated at reflux for 4 hours. Phenylacetylene (10.2g, 0.1 mol) is added over about 30 minutes and heating is continued for 4 hours. After cooling, the reaction mixture is stripped to an oil using a rotary evaporator and reduced pressure. The oil is dissolved in about 100 ml of propionitrile and extracted with four 100-ml portions of cyclohexane. The product is recrystallized from cyclohexane using standard procedures to yield pure 1-phenyl-1,2-dicarba-closo-dodecaborane(12).

EXAMPLE 5

Purification of 1,2-Dicarboxymethyl-1,2-dicarba-closo-dodecaborane(12), $[1,2\text{-}(COOCH_3)\text{-}1,2\text{-}C_2B_{10}H_{10}]$ A 500-ml, three-necked flask is equipped with a mechanical stirrer, reflux condenser, nitrogen inlet and an addition funnel. Decaborane (11.0g, 0.09 mol), acetonitrile (75 ml) and toluene (50 ml) are placed in the flask and the mixture is heated at reflux for 4 hours during which time a solid separates. Dicarboxymethylacetylene (15.0g, 0.10 mol) is added over about 30 minutes and reflux is continued for 20 hours. After cooling to 25° C, the mixture is stripped using a rotary evaporator and reduced pressure to an oil. The oil is dissolved in about 100 ml of acetonitrile and extracted with three 100-ml portions of hexanes. The product is recrystallized using standard techniques from the hexane solution to yield the pure 1,2-dicarboxymethyl-1,2-dicarba-closo-dodecaborane(12).

EXAMPLE 6

Purification of 1-Bromomethyl-1,2-dicarba-closo-dodecaborane(12) $[1\text{-}BrCH_2\text{-}1,2\text{-}C_2B_{10}H_{11}]$ A 500-ml, three-necked flask is equipped with a mechanical stirrer, reflux condenser, nitrogen inlet and an addition funnel. Decaborane (8.85g, 0.07 mol) and acetonitrile (50 ml) are placed in the flask and heated to reflux for 4 hours. Propargyl bromide (11.9g, 0.1 mol) is added over about 1 hour and heating is continued for 18 hours. After cooling, the reaction mixture is extracted with four 50-ml portions of pentane. The combined pentane fractions are washed with two 20-ml portions of 10% sodium hydroxide solution and three 20-ml portions of water. After drying over anhydrous $MgSO_4$, the pentane is removed in vacuo and the product distilled in vacuo to yield pure crystalline 1-bromomethyl-1,2-dicarba-closo-dodecaborane(12).

Although the invention has been illustrated by the preceding examples, it is not to be construed as being limited to the materials employed therein, but rather the invention relates to the generic area as hereinbefore disclosed. Various modifications and embodiments can be made without departing from the spirit and scope thereof.

What is claimed is:

1. A process for the separation and purification of a carborane from a reaction mixture comprised of said carborane and undesirable tarry by-products formed during the reaction of decaborane with an acetylenic compound in the presence of a donor ligand, said process comprising the steps of:
   (a) removing from said mixture any solvent in which said carborane was synthesized except when such solvent:
      (i) also serves as said donor ligand,
      (ii) is employed in amount in excess of the stoichiometric amount required for said reaction, and,
      (iii) is selected from the group consisting of acetonitrile and propionitrile,
   (b) dissolving said mixture from which any solvent has been removed in accordance with step (a) in a first solvent in which all the components of said mixture are soluble and non-reactive therewith,
   (c) extracting said carborane from said mixture with a second solvent, immiscible with the solvent of either steps (a) or (b) and in which said carborane is soluble and said by-products are insoluble, and
   (d) thereafter recovering said carboranes from said second solvent.

2. The process of claim 1 wherein said carborane is an alkyl-substituted carborane.

3. The process of claim 1 wherein said carborane is an aryl-substituted carborane.

4. The process of claim 1 wherein said carborane is a haloalkyl-substituted carborane.

5. The process of claim 1 wherein said carborane is a haloaryl-substituted carborane.

6. The process of claim 1 wherein said donor ligand is acetonitrile and is employed in an amount at least twice that of the required stoichiometric amount.

7. The process of claim 6 wherein said second solvent is a lower alkane.

8. The process of claim 7 wherein said lower alkane is n-hexane.

9. The process of claim 1 wherein said donor ligand is propionitrile and is employed in an amount at least twice that of the required stoichiometric amount.

10. The process of claim 9 wherein said second solvent is a lower alkane.

11. The process of claim 10 wherein said lower alkane is n-decane.

12. The process of claim 9 wherein said second solvent is cyclohexane.

13. The process of claim 1 wherein said first solvent is acetonitrile and said second solvent is a lower alkane.

14. The process of claim 6 wherein said lower alkane is n-hexane.

15. The process of claim 1 wherein said first solvent is propionitrile and said second solvent is n-decane.

16. The process of claim 1 wherein said first solvent is propionitrile and said second solvent is cyclohexane.

17. The process of claim 1 wherein said first solvent is propionitrile and said second solvent is carbon disulfide.

* * * * *